United States Patent [19]

Mosher

[11] Patent Number: 5,525,596
[45] Date of Patent: Jun. 11, 1996

[54] ABSORPTION ENHANCER/SOLUBILIZER COMBINATION FOR IMPROVED BIOAVAILABILITY OF A ZWITTERIONIC COMPOUND

[75] Inventor: Gerold L. Mosher, Lawrence, Kans.

[73] Assignee: Merck & Co., Inc., Rahway, N.J.

[21] Appl. No.: 327,081

[22] Filed: Oct. 21, 1994

[51] Int. Cl.$^6$ .................. A61K 31/55; A61K 31/205; A61K 31/715
[52] U.S. Cl. .................. 514/58; 514/213; 514/556
[58] Field of Search ................... 514/213, 58, 556

[56] References Cited

U.S. PATENT DOCUMENTS 4,537,772  8/1985  Alexander ................... 514/9
5,324,718  6/1994  Loftsson ................... 514/58

*Primary Examiner*—Marianne M. Cintins
*Assistant Examiner*—Phyllis G. Spivack
*Attorney, Agent, or Firm*—Francis P. Bigley; Mark R. Daniel

[57] ABSTRACT

Intestional absorption of zwitterionic compounds is enhanced when the compound is delivered with the absorption enhancer palmitoyl carnitine chloride and the solubilizing agent β-cyclodextrin when compared to delivery with palmitoyl carnitine chloride or β-cyclodextrin alone.

1 Claim, No Drawings

ABSORPTION ENHANCER/SOLUBILIZER COMBINATION FOR IMPROVED BIOAVAILABILITY OF A ZWITTERIONIC COMPOUND

BACKGROUND OF THE INVENTION

The invention relates to novel compositions and methods for enhancing absorption of zwitterionic drugs from the gastrointestinal tract by incorporating therein a mixture of the absorption enhancer palmitoyl carnitine chloride and the solubilizing agent β-cyclodextrin.

Though the gastrointestinal tract is the preferred route for pharmaceutically active compound delivery, all pharmaceutically active compounds are not well absorbed from this site. In many cases, this may be due to the polar nature or hydrophilic character of these pharmaceutically active compounds. Since these compounds are precluded from rapid absorption, such drugs are subject to long residency time in the gastrointestinal environment where both acidic and enzymatic degradation contribute to their poor bioavailability. It is, therefore, clear that any factor which enhances the rate of absorption will demonstrate improved clinical efficacy. In recent years, considerable effort has been directed toward identifying agents which increase gastrointestinal absorption of poorly absorbed compounds. For example, surface active agents (George, Sutter, Finegold, J. Infect. Dis. 136, 822 (1977), chelating agents (Cassidy, Tidball, J. Cell Biol. 32, 672 (1967), salicylates (Higuchi, et al., U.S. Pat. No. 4,462,991 (1984)), anti-inflammatory agents (Yaginuma, et al., Chem. Pharm. Bull. 29, 1974 (1981) and phenothiazines (Alexander and Fix, U.S. Pat. No. 4,425,337 (1984) have been shown to increase gastrointestinal permeability of a variety of drugs. U.S. Pat. Nos. 4,822,733 and 4,537,772 which issued to Alexander, disclose the fact that palmitoyl salts are able to enhance transport of pharmaceutically active compounds from the intestine and into the blood stream.

Although these methods offer improved transport of the pharmaceutically active compound into the blood stream, additional enhancement is often needed. Surprisingly and unexpectedly, Applicant has found that when β-cyclodextrin is added to a formulation of a pharmaceutically active zwitterionic compound and palmitoyl carnitine chloride, a dramatic increase in absorption of the drug from the intestine occurs.

The present use of a combination of palmitoyl carnitine chlorde and β-cyclodextrin to promote gastrointestinal absorption affords several advantages over the prior art's absorption promoting formulations. This novel combination provides greater enhancement and therefore, lower dosages of the pharmaceutically active compounds need to be delivered to the patient. This difference in efficacy further affords opportunities for reducing the required size of the dosage form and potentially minimizing side effects. Enhanced delivery of the pharmaceutically-active ingredient has the additional advantage that absorption does not occur over prolonged intervals during which potentially damaging or irritating compounds might damage the cells which line the intestine. In other words, there is no tissue damage at concentrations of where this combination has been shown to significantly increase drug absorption. In contrast to this, studies have indicated that surfactant activity, with other agents such as sodium lauryl sulfate, is generally associated with some degree of cellular damage. This lack of tissue damage affords a significant advantage to the use of this combination in promoting gastrointestinal drug absorption.

Accordingly, it is an object of this invention to enhance the bioavailability of poorly absorbed pharmaceutically active zwitterionic compounds administered orally or rectally by co-administering these compounds with palmitoyl carnitine chloride and β-cyclodextrin.

A further object of the invention is to provide a new dosage form utilizing a combination of palmitoyl carnitine chloride, β-cyclodextrin and a pharmaceutically active zwitterionic compound which when administered orally or rectally with a therapeutic agent will provide an increased blood level of said therapeutic agent.

Another object of the invention is to provide a formulation which acts as an absorption promoter of gastrointestinal and rectal drug absorption at concentrations which do not alter the normal morphology of the mucosal cells.

Other objects, features and advantages of the invention will be apparent to those skilled in the art from the detailed description of the invention which follows.

All of the foregoing objects are readily attained by providing a composition and method wherein oral and rectal absorption of poorly absorbed pharmaceutically active zwitterionic compounds is enhanced. The method comprises the steps of preparing a dosage form suitable for oral or rectal delivery, the dosage form comprising an effective amount of the poorly absorbed drug, and an effective amount of palmitoyl carnitine chlorde and cyclodextrin.

SUMMARY OF THE INVENTION

A novel pharmaceutical composition for enhancing gastrointestinal tract absorption is presented which comprises a therapeutically effective dosage amount of an orally or rectally administered pharmaceutically active zwitterionic compound administered with palmitoyl carnitne chloride and β-cyclodextrin. A novel method of enhancing the rate of gastrointestinal absorption of an orally or rectally administered pharmaceutically active zwitterionic compound comprising the administration of a therapeutically effective dosage amount of the zwitterionic compound and a combination of palmitoyl carnitine and cyclodctrin is also presented.

DETAILED DESCRIPTION OF THE INVENTION

A novel pharmaceutical composition for enhancing gastrointestinal tract absorption is presented which comprises a therapeutically effective dosage amount of an orally or rectally administered pharmaceutically active zwitterionic compound administered with palmitoyl carnitine chloride and cyclodextrin. A novel method of enhancing the rate of gastrointestinal absorption of an orally or rectally administered pharmaceutically active zwitterionic compound comprising the administration of a therapeutically effective dosage amount of the zwitterionic compound and a combination of palmitoyl carnitine and cyclodctrin is also presented.

By "pharmaceutical composition" is meant, a mixture of ingredients which provides a reliable means of administrating a pharmaceutically active zwitterionic compound. By "pharmaceutically active zwitterionic compound" is meant a zwitterionic compound which is under as or has been shown to function as a medicament.

By "enhancing gastrointestinal tract absorption" is meant that the composition provides for transport of the pharmaceutically active zwitterionic command once given to a human or other animal, from the intestine into the blood stream at a faster rate or to a greater extent than if the pharmaceutically active zwitterionic compound was administered alone or in combination with either palmitoyl carnitine chloride or cyclodextrin alone.

By a "therapeutically effective dosage amount of an orally or rectally administered pharmaceutically active zwitterionic compound" is meant that the amount of the pharmaceutically active zwitterionic compound delivered is sufficient to provide the medicinal effect desired in the human or other animal to which it has been delivered By a "combination of palmitoyl carnitine chloride and cyclodextrin" is meant that both of these compounds are added to the pharmaceutical composition at concentrations which provide for enhanced gastrointestinal tract absorption. The preferred ratio of cyclodextrin to palmitoyl carnitine chloride ranges from about 1 to about 3. The preferred range is from about 1.5 to about 3. The word "about" is used to signify the fact that the exact ratio may vary within normal experimental and manufacturing limits of from 0 to 10%.

Palmitoyl carnitine chloride and cyclodextrin are available commercially from Sigma Chemical Co., St. Louis, Mo. Cyclodextrins are also available from Aldrich Chemical Co., Milwaukee, Wis. The cyclodextrins, also called cycloamyloses, Schardinger dextrins or cycloglucans, are the cyclic oligosaccharides in which the glucose units are linked by a (1–4)glycosidic bonds. α-cyclodextrin contains six glucose units. β-cyclodextrin contains seven glucose units. γ-cyclodextrin contains eight glucose units. The cyclodextrins contain numerous hydroxyl groups that can be derivatized. Common derivatives include alkylates, hydroxy alkylates and esters.

The present invention is also directed to a method of enhancing the rate of gastrointestinal absorption of an orally or rectally administered pharmaceutically active zwitterionic compound. The method generally comprises administering a dosage form capable of being orally or rectally administered, wherein the dosage form comprises a therapeutically effective dosage amount of a poorly absorbed drug, cyclodextrin and palmitoyl carnitine chloride, the cyclodextrin and palmitoyl carnitine chloride being present in the dosage form in sufficient quantity and at a ratio to be effective in enhancing oral and rectal absorption rates of the pharmaceutical active zwitterionic compound.

In addition to palmitoyl carnitine, the following compounds when combined with β-cyclodextrin will provide enhanced transport of a pharmaceutically active compound into the blood stream: lauroylcarnitine, myristoylcarnitine, palmitoylcarnitine, stearoylcarinitine, 2-hexenoylcarinitine, 9-decenoylcarnitine, 9-hexadecenoyls carnitine, alpha-lineoylcarnitine, 2-hydroxylauroylcarnitine, 6-ketodecanoylcarnitine, omega-ethoxycarbonyloctanoylcarnitine, and 2-hydroxypalmitoylcarnitine.

Various pharmaceutically active zwitterionic compounds provide beneficial effects when administered to patients. Such agents which can be made more useful by enhancing their absorption in accordance with this invention, are exemplified by, but not limited to, the following classes of drugs:

(1) Beta-lactam antibiotics such as cefoxitin, N-formamidinyltheinamycin, ampicillin, azlocillin, bacampicillin, cefaclor, cefadroxil, cefatrizine, cefazoline, cefaperazone, ceforanide, cefotaxime, cefotiam, cefroxadine, cefsulodin, cefiazidime, ceftriaxone, ceftizoxime, cephalexin, cephaloglycin, cephaloridine, cephradine, cyclacillin, hetacillin, talampicillin, pivampicillin, and the like;

(2) Angiotensin converting enzyme inhibitor antagonists such as enalapril, and the like;

(3) Amino acids such as methyldopa, carbidopa, levodopa, fludalanine, gamma-aminobutyric acid, and the like;

(4) Smooth muscle relaxants such as theophylline, aminophylline, diphylline, oxtriphylline, ambuphylline, fenethylline, guathylline, pentoxyfylline, xanthinol niacinate, glucophylline and the like;

(5) Polypeptides such as cyclo(N-Ala-Tyr-D-Trp-Lys-Val-Phe)acetate, somatostatin, insulin, gastrin, caerulein, cholecystokinin, and the like;

(6) Anti-inflammatory agents such as indomethacin, and the like;

(7) Diuretics such furosemide and the like; and (8) Echinocandin type antifungals, antiarrhythmics, HIV protease inhibitors, and oxytocin antagonists.

The enhancement of drug absorption in accordance with this invention is not by any means limited to the above drugs, but are in general applicable to other classes of drugs such as analgesics, anabolics, androgens, anorexics, adrenergics, antiadrenergics, antiallergics, anti-bacterials, anticholinergics, antidepressants, antidiabetics, antifungal agents, antihypertensives, antineoplastics, antipsychotics, sedatives, cardiovascular agents, antiulcer agents, anticoagulants, anthelmintics, radio-opaques, radionuclide diagnostic agents, and the like.

The amount of pharmaceutically active zwitterionic compound which will be delivered in this novel composition or using this novel method varies over a wide range, however the therapeutically effective unit dosage amount of the zwitterionic compound depends on that amount known in the art to obtain the desired results.

The composition may also contain other compounds useful in preparing, mixing, blending, dissolving, dispersing, granulating, compressing, or coloring the final formulation.

For oral administration, the formulations may be prepared as liquids, suspensions, capsules, tablets, coated tablets, and other standard procedures known in the art. The preferred formulation is a compressed tablet comprising palmitoyl carnitine, β-cyclodextrin with the pharmacologically required dose of zwitterionic compound and sufficient excipients to formulate an acceptable composition. For rectal application, the formulations may be prepared as microenemas, suppositories, rectal tablets, and other standard procedures known in the art. The preferred formulation is a solid suppository comprising palmitoyl carnitine chloride and β-cyclodextrin with the pharmacologically required dose of zwitterionic compound and sufficient suppository base to formulate an acceptable composition. The methods and choice of excipients and suppository bases are well known to those skilled in the art and the composition of the formulations is not limited to compressed tablets or solid suppositories by this invention.

EXAMPLE 1

Solutions of palmitoyl carnitine, β-cyclodextrin and an [R-(R*,R*)]-3-[(2-hydroxypropyl)amino]-3-methyl-N-[2,3,4,5-tetrahydro-2-oxo-1-[[2'-(H-tetrazol-5-yl)[1,1'-biphenyl]-4-yl]methyl]-1H-1-benzazepin-3-yl]butanamide having the following structure:

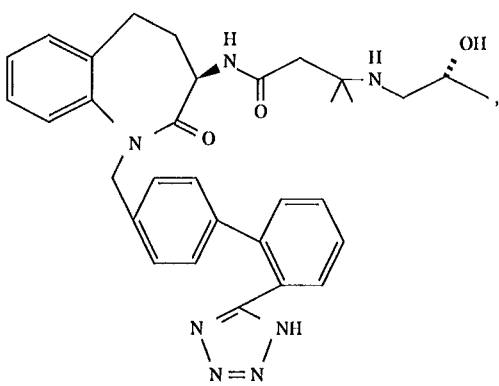

hereinafter referred to as [R-(R*,R*)]-3-[(2-hydroxypropyl)amino]-3-methyl-N-[2,3,4,5-tetrahydro-2-oxo-1-[[2'-(H-tetrazol-5-yl)[1,1'-biphenyl]-4-yl]methyl]-1H-1-benzazepin-3-yl]butanamide were prepared such that [R-(R*,R*)]-3-[(2-hydroxypropyl)amino]-3-methyl-N-[2,3,4,5-tetrahydro-2-oxo-1-[[2'-(H-tetrazol-5-yl)[1,1'-biphenyl]-4-yl]methyl]-1H-1-benzazepin-3-yl]butanamide was maintained at 2 mg/ml. All solutions were prepared in Krebs-Henseleit buffer at Ph 7.4. The solutions were administered to ligated sections of the jejunum of anesthetized rats. Since [R-(R*,R*)]-3-[(2-hydroxypropyl)amino]-3-methyl-N-[2,3,4,5-tetrahydro-2-oxo-1-[[2'-(H-tetrazol-5-yl)[1,1'-biphenyl]-4-yl]methyl]-1H-1-benzazepin-3-yl]butanamide is excreted almost exclusively unchanged in the bile of rats, the bile ducts of the test animals were cannulated for bile collection. The bile was collected in 15 minute intervals for 3.5 hours and analyzed for [R-(R*,R*)]-3-[(2-hydroxypropyl)amino]-3-methyl-N-[2,3,4,5-tetrahydro-2-oxo-1-[[2'-(H-tetrazol-5-yl)[1,1'-biphenyl]-4-yl]methyl]-1H-1-benzazepin-3-yl]butanamide content. From the bile volume, the total amount of drug eliminated could be calculated. After an IV dose, 92% of the drug is found in the bile. Therefore all value were divided by 0.92 to give true absorption values. These values are given in table 1, along with standard deviations which were observed.

TABLE 1

Effect of Palmitoyl Carnitine and β-Cyclodextrin on the Jejunal Absorption of (R-(R*,R*))-3-((2-hydroxypropyl)amino)-3-methyl-N-(2,3,4,5-tetrahydro-2-oxo-1-((2'-(H-tetrazol-5-yl)(1,1'-biphenyl)-4-yl]methyl)1H-1-benzazepin-3-yl]butanamide. Values are % of Dose Absorbed Relative to IV (+/− s.d.)

| Palmitoyl Carnitine | β-Cyclodextrin (mg/kg) | | |
|---|---|---|---|
| Chloride (Mg/kg) | 0 | 7.5 | 15 |
| 0 | 4.98 ± 5.67 | 3.1 ± 1.59 | 12 ± 7.23 |
| 5 | 11.9 ± 2.6 | 13.99 ± 5.4 | 20.44 ± 15.2 |
| 10 | 22.6 ± 13.5 | 29.6 ± 8.2 | 49.28 ± 13.4 |

EXAMPLE 2

Powders were prepared so as to contain in each dose, 2 mg/kg of [R-(R*,R*)]-3-[(2-hydroxypropyl)amino]-3-methyl-N-[2,3,4,5-tetrahydro-2-oxo-1-[[2'-(H-tetrazol-5-yl)[1,1'-biphenyl]-4-yl]methyl]-1H-1-benzazepin-3-yl]butanamide, 0–10 mg/kg palmitoyl carnitine chloride, 0–15 mg/kg β-cyclodextrin and microcrystalline cellulose. The powders were administered to unligated sections of the jujunum of anesthetized rats. Bile was collected and the absorption of [R-(R*,R*)]-3-[( 2-hydroxypropyl)amino]-3-methyl-N-[2,3,4,5-tetrahydro-2-oxo-1-[[2'-(H-tetrazol-5-yl)[1,1'-biphenyl]-4-yl]methyl]-1H-1-benzazepin-3-yl]butanamide was determined as in Example 1. The results of these studies are provided in Table 2, along with observed standard deviations.

TABLE 2

| Palmitoyl Carnitine | β-Cyclodextrin (mg/kg) | | |
|---|---|---|---|
| Chloride (mg/kg) | 0 | 7.5 | 15 |
| 0 | 0.18 ± 0.26 | | |
| 10 | 3.3 ± 1.9 | 8.9 ± 7.6 | 14.8 ± 9.8 |

EXAMPLE 3

Lyophilized preparations of [R-(R*,R*)]-3-[(2-hydroxypropyl)amino]-3-methyl-N-[2,3,4,5-tetrahydro-2-oxo-1-[[2'-(H-tetrazol-5-yl)[1,1'-biphenyl]-4-yl]methyl]-1H-1-benzazepin-3-yl]butanamide were prepared from solutions containing 2 mg/ml of [R-(R*,R*)]-3-[(2-hydroxypropyl)amino]-3-methyl-N-[2,3,4,5-tetrahydro-2-oxo-1-[[2'-(H-tetrazol-5-yl)[1,1'-biphenyl]-4-yl]methyl]-1H-1-benzazepin-3-yl]butanamide and 15 mg/ml of β-cyclodextrin or 20 mg/ml hydroxypropyl-β-cyclodextrin. The lyophilized preparations were mixed with palmitoyl carnitine chloride and microcrystalline cellulose and compressed into tablets. The tablets contained 2 mg/kg of [R-(R*,R*)]-3-[(2-hydroxypropyl)amino]-3 -methyl -N-[2,3,4,5,-tetrahydro-2-oxo-1-[[2'-(H-tetrazol-5-yl)[1,1'biphenyl]-4-yl]methyl-1H1-benzazepin-3-yl]butanamide and 10 mg/kg palmitoyl carnitine chloride. The tablets were administered to the unligated sections of the jejunum of anesthetized rats. Bile was collected and the absorption of [R-(R*,R*)]-3-[(2-hydroxypropyl) amino]-3 -methyl -N- [2,3,4,5 -tetrahydro-2-oxo-1-[[2'-(H-tetrazol-5-yl)[1,1'-biphenyl]-4-yl]methyl]-1H-1-benzazepin-3-yl]butanamide determined as in Example 1. The percentage absorption of [R-(R*,R*)]-3-[(2-hydroxypropyl)amino]-3-methyl-N-[2,3,4,5-tetrahydro-2-oxo-1-[[2'-(H-tetrazol-5-yl)[1,1'-biphenyl]-4-yl]methyl]-1H-1-benzazepin-3-yl]butanamide from the lyophilized formulation containing β-cyclodextrin was 28.2±18.3 and from the hydroxpropyl-β-cyclodextrin, 7.5±6.2.

EXAMPLE 4

Fifteen parts of water were added to a mixture of [R-(R*,R*)]-3-[(2-hydroxypropyl)amino]-3-methyl-N-[2,3,4,5-tetrahydro-2-oxo-1-[[2'-(H-tetrazol-5-yl)[1,1'-biphenyl]-4-methyl]- 1H-1-benzazepin-3-yl]butanamide, β-cyclodextrin, palmitoyl carnitine chloride, micro-crystalline cellulose and starct (2:15:10:15:10). The preparation was extruded through a screen (1 micron openings) and spheronized. After drying, the beads were administered to unligated sections of the jejunum of anesthetized rats. Bile was collected and the absorption of [R-(R *,R *)]-3-[(2-hydroxypropyl)amino]-3-methyl-N-[2,3,4,5-tetrahydro-2-oxo- 1-[[2'-(H-tetrazol-5-yl)[1,1'-biphenyl]-4-yl]methyl]-1H-1-benzazepin-3-yl]butanamide determined in Example 1. The absorption of [R-(R*,R*)]-3-[(2-hydroxypropyl)amino]-3-methyl-N-[2,3,4,5-tetrahydro-2-oxo-1-[[2'-(H-tetrazol-5-yl)[1,1'-biphenyl]-4-yl]methyl]-1H-1-benzazepin- 3-yl]butanamide was found to be 8.8%±4.28%.

EXAMPLE 5

Compressed tablets were prepared with and without 112 mg β-cyclodextrin (7.5 mg/kg), containing 15 mg of [R-(R*, R*)]-3-[(2-hydroxypropyl)amino]-3-methyl-N-[2,3,4,5-tetrahydro-2-oxo-1[[2'-(H-tetrazol-5-yl)[1,1'-biphenyl]-4-yl]methyl]-1H-1-benzazepin-3-yl]butanamide (1 mg/kg) and 150 mg palmitoyl carnitine chloride (10 mg/kg) in a tablet matrix containing 203 mg microcrystalline cellulose, 100 mg lactose, 20 mg corn starch and 2 mg magnesium stearate. The tablets were administered to the duodenum of dogs through a surgically prepared fistual. Serial blood samples were taken from the dogs for four hours after dosing and analyzed for [R-(R*,R*)]-3-[(2-hydroxypropyl)amino]-3-methyl-N -[2,3,4,5-tetra-hydro-2-oxo-1-[[2'-(H-tetrazol-5-yl)[1,1'-biphenyl]-4-yl]methyl]-1H-1-benzazepin-3-yl] butanamide. The results given as resulting area under [R-(R*,R*)]-3-[(2-hydroxy-propyl)amino] -3-methyl-N-[2,3,4,5-tetrahydro-2-oxo- 1-[[2'-(H-tetrazol-5-yl)[1,1'-biphenyl]-4-yl]methyl]-1H-1-benzazepin-3-yl]butanamide concentration-time curve ± standard deviations, are 361±168 ng min/ml in the absence of β-cyclodextrin and 1186±491 mg min/ml in the presence of β-cyclodextrin.

EXAMPLE 6

Fifteen parts of water are added to a mixture of [R-(R*,R*)]-3-[(2-hydroxypropyl)amino]-3-methyl-N-[2,3,4,5-tetrahydro-2-oxo-1-[[2'-(H-tetrazol-5-yl)[1,1'-biphenyl]-4-yl]methyl]-1H-1-benzazepin-3-yl]butanamide, β-cyclodextrin, palmitoyl carnitine chloride, micro-crystalline cellulose and starch (1:5:10:15:10). The preparation is extruded through a screen (2 micron openings) and spheronized. After drying the beads are spray coated with cellulose acetate phthalate in a fluidized bed coater. After further drying the beads are filled into hard gelatin capsules.

EXAMPLE 7

[R-(R *,R *)]-3-[(2-hydroxypropyl)amino]-3-methyl-N-[2,3,4,5-tetrahydro-2-oxo-1-[[2'-(H-tetrazol-5-yl)[1,1'-biphenyl]-4-yl]methyl]-1H-1-benzazepin-3-yl]butanamide, β-cyclodextrin, palmitoyl carnitine chloride and flowable styarch are blended in the ratio (1:4:2:1.5). The blend is wet granulated with water, dried and filled into capsules.

What is claimed is:

1. A pharmaceutical composition for enhancing gastroinestinal tract absorption comprising a therapeutically effective dosage amount of (R-(R*,R*))-3-((2-hydroxypropyl)amino)-3-methyl-N-2,3,4,5-tetrahydro-2-oxo-1-((2'-(H-tetrazol-5-yl)(1,1'-biphenyl)-4-yl]methyl)1H-1-benzazepin-3-yl]butanamide, palmitoyl carnitine chloride and cyclodextrin.

* * * * *